United States Patent
Haak et al.

Patent Number: 5,464,387
Date of Patent: Nov. 7, 1995

[54] TRANSDERMAL DELIVERY DEVICE

[75] Inventors: Ronald P. Haak, Menlo Park; Felix Theeuwes, Los Altos Hills; J. Richard Gyory, San Jose, all of Calif.; Gary A. Lattin, Forest Lake, Minn.

[73] Assignee: Alza Corporation, Palo Alto, Calif.

[21] Appl. No.: 330,031

[22] Filed: Oct. 27, 1994

Related U.S. Application Data

[63] Continuation-in-part of Ser. No. 194,783, Feb. 10, 1994, abandoned, which is a continuation of Ser. No. 969,661, Oct. 30, 1992, abandoned, which is a division of Ser. No. 735,126, Jul. 24, 1991, Pat. No. 5,203,768.

[51] Int. Cl.$^6$ .................................................. A61N 1/30
[52] U.S. Cl. ............................................ 604/20; 604/890.1
[58] Field of Search .......................... 604/890.1, 891.1, 604/20, 26, 49; 128/898, 798, 799, 802, 803

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 3,991,755 | 11/1976 | Vernon et al. | 128/172.1 |
| 4,141,359 | 2/1979 | Jacobsen et al. | 128/172.1 |
| 4,144,317 | 3/1979 | Higuchi et al. | 424/21 |
| 4,250,878 | 2/1981 | Jacobsen et al. | 128/207.21 |
| 4,286,592 | 9/1981 | Chandrasekaran | 128/260 |
| 4,314,557 | 2/1982 | Chandrasekaran | 128/260 |
| 4,379,454 | 4/1983 | Campbell et al. | 604/897 |
| 4,383,529 | 5/1983 | Webster | 604/20 |
| 4,398,545 | 8/1983 | Wilson | 128/798 |
| 4,474,570 | 10/1984 | Ariura et al. | 604/20 |
| 4,568,343 | 2/1986 | Leeper et al. | 604/897 |
| 4,640,689 | 2/1987 | Sibalis | 604/20 |
| 4,702,732 | 10/1987 | Powers et al. | 604/20 |
| 4,722,726 | 2/1988 | Sanderson et al. | 604/20 |
| 4,731,049 | 3/1988 | Parsi | 604/20 |
| 4,744,787 | 5/1988 | Phipps et al. | 604/20 |
| 4,747,819 | 5/1988 | Phipps et al. | 604/20 |
| 4,752,285 | 6/1988 | Petelenz et al. | 604/20 |
| 4,808,152 | 2/1989 | Sibalis | 604/20 |
| 4,878,892 | 11/1989 | Sibalis | 604/20 |
| 4,927,408 | 5/1990 | Haak et al. | 604/20 |
| 4,940,456 | 7/1990 | Sibalis | 604/20 |
| 5,084,006 | 1/1992 | Lew et al. | 604/20 |
| 5,125,894 | 6/1992 | Phipps | 604/20 |
| 5,135,477 | 8/1992 | Untereker et al. | 604/20 |
| 5,162,042 | 11/1992 | Gyory et al. | 604/20 |
| 5,167,616 | 12/1992 | Haak et al. | 604/20 |
| 5,203,768 | 4/1993 | Haak et al. | 604/20 |

FOREIGN PATENT DOCUMENTS 410009  5/1934  Switzerland .

OTHER PUBLICATIONS

Abramson and Gorin, J. Phys. Chem. 44, pp. 1094–1102 (1940).

Dorland's Illustrated Medical Dictionary.

*Primary Examiner*—C. Fred Rosenbaum
*Assistant Examiner*—Chalin Smith
*Attorney, Agent, or Firm*—D. Byron Miller; Edward L. Mandell; Steve F. Stone

[57] ABSTRACT

A transdermal drug delivery device (20) is provided having both an active drug reservoir (24) and a passive drug reservoir (26). Drug is actively delivered by iontophoresis from the active drug reservoir (24) by an electric field generated by a power source (21). Simultaneously, drug is delivered from passive reservoir (26) by passive (i.e., non-electrically assisted) diffusion. In one embodiment, the passive drug reservoir (26) is electrically insulated from the active drug reservoir (24). In a second embodiment, both the active and the passive drug are contained in the same reservoir (34). In the second embodiment, the active drug is ionizable while the passive drug is non-ionizable. Most preferably, the active drug is an ionizable form (i.e., a salt form) of the passive drug.

26 Claims, 1 Drawing Sheet

TRANSDERMAL DELIVERY DEVICE

RELATED CASES

This case is a continuation-in-part of U.S. Ser. No. 08/194,783, filed Feb. 10, 1994 now abandoned, which is a continuation of U.S. Ser. No. 07/969,661, filed Oct. 30, 1992, now abandoned; which is a division of U.S. Ser. No. 07/735,126, filed Jul. 24, 1991, now U.S. Pat. No. 5,203,768.

TECHNICAL FIELD

This invention relates to a device for delivering an agent transdermally or transmucosally. More particularly, this invention relates to such a delivery device which delivers an agent both passively (i.e., by diffusion) and actively using electrical power.

BACKGROUND ART

The transdermal route of parenteral delivery of drugs provides many advantages over other administrative routes. Passive transdermal systems which deliver a wide variety of agents by the physical process of diffusion are described in U.S. Pat. Nos. 3,598,122; 3,598,123; 4,286,592; 4,314,557; 4,379,454 and 4,568,343, for example, all of which are incorporated herein by reference. A passive system in its simplest form consists of a polymeric reservoir having the agent to be delivered dispersed therethrough. The agent diffuses through the reservoir, across the reservoir-biological surface interface, and subsequently across the biological surface. When the biological surface is human skin, the stratum corneum layer of the skin is a complex barrier due to a chemical keratin-phospholipid complex which acts along with the horny layer as a barrier to the penetration of drugs into the body. The stratum corneum is known to both a lipophilic phase as well as a hydrophilic phase. In general, passive drug delivery involves the diffusion of drugs through the lipophilic phase of the stratum corneum and the underlying layers of the skin. As used herein, the term "passive" is defined as meaning drug delivery by diffusion and without electrical assistance. The term "biological surface" as used herein, is defined as including without limitation, skin, mucosal membranes, nails and blood vessel walls. In general, it is preferable to passively deliver non-ionized drugs and agents using a passive transdermal delivery system since ionized drugs and agents usually are unable to passively permeate through human skin at therapeutically effective rates.

A more recent method of transdermal drug delivery uses electrical current to actively transport agents across a biological surface. This concept is based upon basic principles of electrochemistry and is referred to herein as electrically assisted or iontophoretic delivery. Abramson and Gorin in J. Phys. Chem. 44, pp 1094–1102 (1940) showed that charged ions can be introduced into the skin under the influence of an electric field and that the pathways for transdermal ion transport are hydrophilic pathways in the skin. These hydrophilic pathways include the sweat glands and hair follicles. Thus, although both passive delivery devices and electrically-assisted delivery devices involve drug delivery through the skin, the transdermal pathways for drugs delivered from passive devices and electrically-assisted devices are quite different.

Iontophoresis, according to Dorland's Illustrated Medical Dictionary, is defined to be "the introduction, by means of electric current, of ions of soluble salts into the tissues of the body for therapeutic purposes."

Iontophoretic devices have been known since the early 1900's. British patent specification No. 410,009 (1934) described an iontophoretic device which overcame one of the disadvantages of such early devices known to the art at that time, namely the requirement of a special low tension (low voltage) source of current which meant that the patient needed to be immobilized near such source. The device of that British specification was made by forming a galvanic cell from the electrodes and the material containing the medicament or drug to be delivered transdermally. The galvanic cell produced the current necessary for iontophoretically delivering the medicament. This ambulatory device thus permitted iontophoretic drug delivery with substantially less interference with the patient's daily activities.

More recently, a number of United States patents have issued in the iontophoresis field, indicating a renewed interest in this mode of drug delivery. For example, Vernon et al U.S. Pat. No. 3,991,755; Jacobsen et al U.S. Pat. No. 4,141,359; Wilson U.S. Pat. No. 4,398,545; and Jacobsen U.S. Pat. No. 4,250,878 disclose examples of iontophoretic devices and some applications thereof. The iontophoresis process has been found to be useful in the transdermal administration of medicaments or drugs including lidocaine hydrochloride, hydrocortisone, fluoride, penicillin, dexamethasone sodium phosphate, insulin and many other drugs. Perhaps the most common use of iontophoresis is in diagnosing cystic fibrosis by delivering pilocarpine salts iontophoretically. The pilocarpine stimulates sweat production; the sweat is collected and analyzed for its chloride content to detect the presence of the disease.

In presently known iontophoretic devices, at least two electrodes are used. Both of these electrodes are disposed so as to be in intimate electrical contact with some portion of the skin of the body. One electrode, called the active or donor electrode, is the electrode from which the ionic substance, medicament, drug precursor or drug is delivered into the body by electromigration (i.e., the movement of charged ions within an electric field imposed across the body surface). The other electrode, called the counter, indifferent, inactive or return electrode, serves to close the electrical circuit through the body. In conjunction with the patient's skin contacted by the electrodes, the circuit is completed by connection of the electrodes to a source of electrical energy, e.g., a battery. For example, if the ionic substance to be delivered into the body is positively charged (i.e., a cation), then the anode will be the active electrode and the cathode will serve to complete the circuit. If the ionic substance to be delivered is negatively charged (i.e., an anion), then the cathode will be the active electrode and the anode will be the counter electrode.

Alternatively, both the anode and cathode may be used to deliver drugs of opposite charge into the body. In such a case, both electrodes are considered to be active or donor electrodes. For example, the anode can deliver a positively charged ionic substance into the body while the cathode can deliver a negatively charged ionic substance into the body.

It is also known that iontophoretic delivery devices can be used to deliver an uncharged drug or agent into the body. This is accomplished by a process called electroosmosis. Electroosmosis is the transdermal flux of a liquid solvent (e.g., the liquid solvent containing the uncharged drug or agent) which is induced by the presence of an electric field imposed across the skin by the donor electrode. As used herein, the terms "iontophoresis" and "iontophoretic" refer to (1) the delivery of charged drugs or agents by electromigration, (2) the delivery of uncharged drugs or agents by the process of electroosmosis, (3) the delivery of charged drugs or agents by the combined processes of electromigration and electroosmosis, and/or (4) the delivery of a mixture of charged and uncharged drugs or agents by the combined processes of electromigration and electroosmosis.

As with passive transdermal delivery systems, iontophoretic delivery devices also require a reservoir or source of the beneficial agent to be delivered into the body. In general, it is preferable to deliver ionized drugs and agents using an iontophoretic delivery device. Examples of such reservoirs or sources of ionized or ionizable agents include a pouch as described in the previously mentioned Jacobsen U.S. Pat. No. 4,250,878, or a pre-formed gel body as described in Webster U.S. Pat. No. 4,383,529 and Ariura et al U.S. Pat. No. 4,474,570. Such drug reservoirs are electrically connected to the anode or the cathode of an iontophoresis device to provide a fixed or renewable source of one or more desired agents.

More recently, iontophoretic delivery devices have been developed in which the donor and counter electrode assemblies have a "multi-laminate" construction. In these devices, the donor and counter electrode assemblies are formed of multiple layers of (usually) polymeric matrices. For example, Parsi U.S. Pat. No. 4,731,049 discloses a donor electrode assembly having hydrophilic polymer based electrolyte reservoir and drug reservoir layers, a skin-contacting hydrogel layer, and optionally one or more semipermeable membrane layers. Sibalis U.S. Pat. No. 4,640,689 discloses in FIG. 6 an iontophoretic delivery device having a donor electrode assembly comprised of a donor electrode (204), a first drug reservoir (202), a semipermeable membrane layer (200), a second drug reservoir (206), and a microporous skin-contacting membrane (22'). The electrode layer can be formed of a carbonized plastic, metal foil or other conductive films such as a metallized mylar film. In addition, Ariura et al, U.S. Pat. No. 4,474,570 discloses a device wherein the electrode assemblies include a conductive resin film electrode layer, a hydrophilic gel reservoir layer, a current distribution and conducting layer and an insulating backing layer. Ariura et al disclose several different types of electrode layers including an aluminum foil electrode, a carbon fiber non-woven fabric electrode and a carbon-containing rubber film electrode.

Transdermal iontophoretic delivery devices having electrodes composed of electrochemically inert materials, as well as devices having electrodes composed of electrochemically reactive materials are known. Examples of electrochemically inert electrode materials include platinum, carbon, gold and stainless steel. The prior art has also recognized that the electrochemically reactive electrode materials are in many cases preferred from the standpoint of drug delivery efficiency and pH stability. For example, U.S. Pat. Nos. 4,744,787; 4,747,819 and 4,752,285 all disclose iontophoretic electrodes composed of materials which are either oxidized or reduced during operation of the device. Particularly preferred electrode materials include silver as the anodic electrode, and silver chloride as the cathodic electrode.

A primary advantage of passive transdermal delivery systems over electrically assisted iontophoretic delivery devices is cost. Because passive systems do not require any source of electrical power and the attendant electrical circuitry, the cost of a passive system is significantly less than an electrically powered iontophoretic delivery device adapted to deliver the same drug. Passive systems are also typically much easier to manufacture in part because of their simpler construction and lack of any electrical components. On the other hand, passive systems can only be used to deliver those drugs which are able to permeate through skin at pharmacologically effective rates. Because human skin presents a significant barrier to passive drug permeation, relatively few drugs have been found to be suitable for passive delivery systems.

Electrically assisted iontophoretic delivery devices on the other hand have the ability to deliver many drugs at therapeutically effective rates, including drugs having high molecular weights such as polypeptides and proteins, which cannot be delivered at therapeutically effective rates by passive transdermal delivery systems. In addition, electrically assisted iontophoretic delivery devices provide other advantages over passive transdermal delivery systems. One advantage is the shorter time required to reach pharmacologically effective transdermal drug delivery rates. Electrically assisted devices can achieve pharmacologically effective transdermal delivery rates within several minutes of start-up whereas passive transdermal delivery systems typically require much longer start-up periods. A second advantage of electrically assisted iontophoretic delivery devices is the degree of control over the amount and rate of drug delivered from the device, which can be achieved simply by controlling the level of electrical current applied by the device. A third advantage of electrically-assisted iontophoretic delivery devices is their ability to be programmed to deliver drug at a predetermined regimen and their ability to deliver either a bolus dose or to deliver medication "on demand" in applications such as the delivery of narcotic analgesics for treatment of pain. Passive transdermal delivery systems do not have these active control features and simply deliver drug at a rate predetermined by the design of and the materials used in, the passive system.

It is therefore an object of this invention to provide a transdermal delivery device having the advantages of a passive transdermal delivery system and the advantages of an electrically assisted iontophoretic delivery device.

In particular, it is an object of the present invention to provide a transdermal delivery device, at least a portion of which is electrically powered and capable of delivering an agent transdermally by iontophoresis, and therefore able to deliver drugs transdermally at therapeutically effective rates with a minimal start-up time and in preprogrammed or on demand delivery regimens.

It is a further object of the present invention to provide a transdermal agent delivery device, at least a portion of which delivers drugs transdermally by passive non-electrically assisted delivery and which is able to deliver agent without consuming electrical power.

DISCLOSURE OF THE INVENTION

These and other important objects of the present invention are met by a transdermal agent delivery device including an active agent reservoir which is adapted to be placed in active agent transmitting relation with a body surface. The active agent reservoir is positioned within an electric field generated by a source of electrical power which is electrically connected to the active agent reservoir. The delivery device also includes a passive agent reservoir adapted to be placed in passive agent transmitting relation to a body surface. The passive agent contained in the passive agent reservoir is able to passively diffuse through the passive agent reservoir and through the body surface. In one embodiment of the invention, the passive agent reservoir is electrically insulated from the electrical field generated by the power source. When placed on a body surface, the device delivers active agent by iontophoresis and passive agent by diffusion.

In another embodiment of the invention, the active agent and the passive agent are present in the same reservoir, which combined active agent and passive agent reservoir is positioned within an electric field generated by a source of electrical power which is electrically connected to the agent reservoir. In this embodiment, the active agent is in the form of charged ions which are delivered by the electric field by the process of electromigration. The passive agent is non-ionized and is delivered primarily by passive diffusion.

MODES FOR CARRYING OUT THE INVENTION

Figure 1:
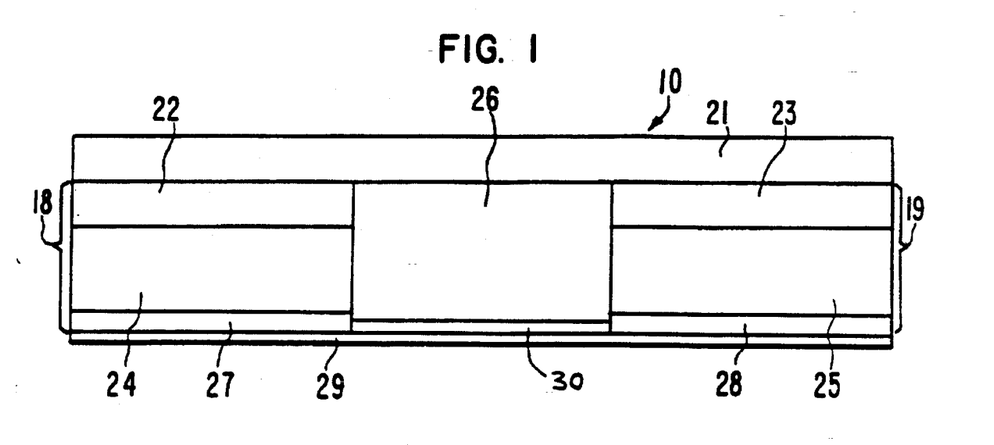
FIG. 1 is a schematic view of a transdermal drug delivery device according to the present invention.

FIG. 1 is a schematic view of a delivery device 10 for delivering a beneficial agent through a body surface such as intact skin or a mucosal membrane. Delivery device 10 includes an iontophoretic donor electrode assembly 18 and an iontophoretic counter electrode assembly 19. Electrode assemblies 18 and 19 are connected in series by top layer 21 which contains an electrical power source, typically one or more low voltage batteries, and an optional control circuit (e.g., a resistor, a transistor-based current control circuit, an on-off switch and/or a microprocessor) adapted to control the current output of the power source over time. When the device 10 is in storage, no current flows because the device does not form a closed circuit. When the device 10 is placed on the skin or mucosal membrane of a patient and the electrode assemblies 18 and 19 are hydrated, the circuit between the electrodes is closed and the power source begins to deliver current through the device and through the body of the patient. The donor and counter electrode assemblies 18 and 19 are adhered to the skin by means of ion-conducting adhesive layers 27 and 28. The device also includes a strippable release liner 29 which is removed just prior to application to the body. As an alternative to the ion-conducting adhesive layers 27 and 28 shown in FIG. 1, the iontophoretic delivery device 10 may be adhered to the skin using a peripheral adhesive means, i.e. an adhesive positioned along the periphery of device 10, e.g., surrounding electrode assemblies 18 and 19. One example of a peripheral adhesive means is an adhesive overlay. Any of the conventional adhesive overlays used to secure passive transdermal delivery devices to the skin may be used. Other examples of peripheral adhesive means are disclosed in Phipps et al U.S. Pat. No. 5,125,894 (adhesive layers 25 and 26 in FIG. 2 and peripheral adhesive 116 in FIG. 3); and Lattin et al WO 94/15669 (undersurface of sheet 20 shown in FIG. 2 is coated with a contact adhesive), the disclosures of which are incorporated herein by reference.

The donor electrode assembly 18 includes a donor electrode 22 and an active agent reservoir 24. The active agent reservoir 24 contains the beneficial agent to be iontophoretically delivered by device 10. The counter electrode assembly 19 includes a counter electrode 23 and an electrolyte reservoir 25. The electrolyte reservoir 25 contains a suitable pharmacologically acceptable salt. At the time of use, the active agent in reservoir 24 and the electrolyte in reservoir 25 are in the form of a liquid (e.g., aqueous) solution or suspension. Suitable electrolytes include sodium chloride, alkali metal salts, alkaline earth metal salts such as chlorides, sulfates, nitrates, carbonates, phosphates, and organic salts such as ascorbates, citrates, acetates and mixtures thereof. Reservoir 25 may also contain a buffering agent. Sodium chloride is a suitable electrolyte when the counter electrode 23 is the cathode and is composed of silver/silver chloride, optionally with a sodium phosphate buffer. The donor and counter electrode assemblies 18 and 19 are physically attached to, and separated by, a reservoir 26 and form a single self-contained unit therewith.

Reservoir 26 performs two functions. In connection with the iontophoretic electrode assemblies 18 and 19 of device 10, reservoir 26 acts as an insulator between electrodes assemblies 18 and 19. Because reservoir 26 is in intimate contact with both the active agent reservoir 24 and the electrolyte reservoir 25, the reservoir 26 must be substantially impermeable to the free passage of ionic species. In this way, reservoir 26 prevents the electrode assemblies 18 and 19 from short circuiting by preventing direct electrical and/or ion transport between the electrode assemblies 18 and 19. Accordingly, reservoir 26 is formed of a material which is substantially impermeable to the passage of ions. Reservoir 26 is preferably formed of a hydrophobic non-conducting polymeric material which is impermeable to both the passage of ions and water. Most preferably the matrix of reservoir 26 is formed of an ethylene vinyl acetate copolymer.

In addition, reservoir 26 may also function as the reservoir for the passive agent. This function will be described in more detail hereinafter.

Electrodes 22 and 23 are electrically conductive and may be formed of a metal, e.g., a metal foil or metal deposited or painted on a suitable backing. Examples of suitable metals include silver, zinc, silver/silver chloride, aluminum, platinum, stainless steel, gold and titanium. Alternatively, the electrodes 22 and 23 may be formed of a hydrophobic polymer matrix containing a conductive filler such as a metal powder, powdered graphite, carbon fibers or other known electrically conductive filler material. The hydrophobic polymer based electrodes may be made by mixing the conductive filler in the hydrophobic polymer matrix. For example, zinc powder, silver powder, silver/silver chloride powder, powdered carbon, carbon fibers and mixtures thereof can be mixed in a hydrophobic polymer (e.g., a polyisobutylene rubber) matrix, with the preferred amount of conductive filler being within the range of about 30 to 90 vol % and the remainder being the hydrophobic polymer matrix.

Electrodes 22 and 23 are electrically connected to the power source in layer 21 using well known means, e.g., printed flexible circuits, metal foils, wires, electrically conductive adhesives or by direct contact. As an alternative to a battery as the power source, device 20 can be powered by a galvanic couple formed by the donor electrode 22 and counter electrode 23 being composed of dissimilar electrochemical couples and being placed in electrical contact with one another. Typical galvanic couple materials for delivering a cationic agent include a zinc donor electrode 22 and a silver/silver chloride counter electrode 23. A Zn-Ag/AgCl galvanic couple provides an electrical potential of about 1 volt.

Regardless of the source of electrical power used, the power source in combination with the electrode assemblies 18 and 19 and the patient's body completes the circuit and generates an electrical field across the body surface (e.g., skin) to which device 10 is applied. This electrical field runs from the power source in layer 21, through the electrode 22, through the active agent reservoir 24, through the adhesive layer 27, through the body of the patient, through the adhesive layer 28, through the electrolyte reservoir 25, through the electrode 23 and back to the power source in layer 21. The electric field generated by the power source causes active agent ions within reservoir 24 to be delivered through adhesive layer 27 and into the body by the process of electromigration.

In the embodiment shown in FIG. 1, the passive reservoir 26 is electrically insulated from the electric field generated by the power source in layer 21. Passive reservoir 26 may be insulated from the electric field by any number of conventional means. The most preferred way of isolating the passive agent from the electric field is to choose an electrically insulating material as the matrix for passive reservoir 26. Most preferably, the matrix of reservoir 26 is comprised of a hydrophobic polymer such as polyisobutylene or ethylene vinyl acetate. These hydrophobic polymers do not hold water, water being the preferred solvent for solubilizing drug salts delivered iontophoretically, and therefore hydrophobic polymers do not allow transport of ions therethrough and thereby act as electrical insulators.

Alternatively, the passive reservoir 26 may be composed of a conductive matrix, such as a hydrophilic polymer, which has an insulating layer separating the passive agent reservoir 26 from the active agent reservoir 24, the electrolyte reservoir 25, the electrodes 22 and 23 and the ion-conducting adhesive layers 27 and 28 (if present). The insulating layer can be a layer of a hydrophobic polymer (e.g., polyethylene) or simply a space which separates the passive reservoir 26 from the current conducting portions of the device and thereby prevents current from passing directly from electrodes 22 and reservoir 24, through passive reservoir 26, to electrode 23 and reservoir 25. In either case, no electrical current passes through passive reservoir 26 and the passive agent within reservoir 26 is not subject to any electric field effects when the device 10 applies current through the body.

Reservoir 26 contains a passive agent adapted to be delivered into the body surface without electrical assistance. Those skilled in the art will appreciate that reservoir 26 may take other geometric configurations besides the means separating reservoirs 24 and 25. For example, the passive reservoir may be arranged to completely surround reservoirs 24 and 25, optionally with a portion thereof physically separating reservoirs 24 and 25. Thus, the peripheral adhesive means described earlier can function as the passive reservoir as long as the passive agent is compatable with the adhesive. Any number of other geometric configurations are possible as long as passive reservoir 26 is insulated from the electric field generated by the device and is able to be placed in passive agent transmitting relation with the body surface (e.g., skin). The passive agent reservoir 26, in addition to being insulated from the electric field generated by the power source, must also be permeable to the passive (i.e., non-electrically assisted) diffusion of the passive agent therethrough. Thus, the passive agent reservoir matrix is made from a material in which the passive agent is soluble and/or the passive agent reservoir matrix is microporous and has a structure that enables the passive agent to pass through the pre-existing pores or capillaries, either by diffusive permeability or microporous hydrodynamic flow.

Because the delivery of passive agent is not affected by the electric field generated by the power source, the passive agent delivery rate will be substantially independent of the amount of current applied by the device and will not be affected by the activation or the deactivation of the electrically assisted portions of the device. In this manner, the passive agent reservoir may be used to provide a baseline delivery of drug or other beneficial agent to the patient. The baseline delivery rate may then be supplemented by activating the electrically assisted portions of the device.

In order to control the passive agent delivery rate, it is possible to adjust the concentration of passive agent in the reservoir matrix. Alternatively, the composition or form of the matrix material can be chosen in accordance with well known principles. For example, if a constant passive drug delivery rate is required, it is generally preferable to provide an amount of passive agent in excess of saturation concentration in the passive reservoir matrix. In many cases, the skin itself provides a suitable limit on the maximum rate at which drug is passively delivered from reservoir 26 into the body. In those cases where a lower passive delivery rate is desired, an optional flux control membrane 30 (e.g., a microporous membrane) may be provided on the skin side of the passive agent reservoir 26 which exhibits a passive agent flux which is less than the flux through the body surface to which the device 10 is applied.

As is known in the art, the selection of appropriate materials for controlling the passive agent flux through either the membrane 30 or the passive agent reservoir matrix material will be dependent on the particular passive agent to be delivered from reservoir 26. Both organic and inorganic polymeric materials can be shaped into a wide variety of forms with tailored morphology and a wide range of chemical and physical properties to advantageously control release of a wide variety of agents, including those with large molecular structures such as peptides and proteins, and over a large dosage rate range. In the case of microporous matrix or membrane materials, by impregnating the interconnected pores of the microporous structure with a diffusive medium for the passive agent to be administered, a given microporous membrane or matrix material can be adapted to control the release of agents having a wide range of chemical properties by diffusive permeability. Thus, by varying the concentration of passive agent in the reservoir 26, as well as the composition, pore size, and effective thickness of the rate controlling matrix or membrane material, the viscosity of the drug to be administered by appropriate formulation or by impregnating the material with suitable solvent, the dosage rate per area of passive agent reservoir 26 can be controlled since the material functions to meter the flow of drug from the device. Therefore, passive agent reservoirs having the same surface area can provide different dosages of a passive agent by varying the above discussed parameters in accordance with well known principles.

Suitable matrices for the passive agent reservoir 26 and/or the membrane 30 include, without limitation, natural and synthetic rubbers such as polybutylene, polyisobutylene, polybutadiene, polyethylene, styrenebutadiene, copolymers, polyisoprene, polyurethane, ethylene/propylene copolymers, polyalkylacrylate polymers, copolyesters, ethylene/acrylic copolymers, silicones, butadiene/acrylonitrile copolymers, skin contact adhesive matrices such as silicone and polyisobutylene adhesives, and ethylene vinylacetate (EVA) polymers described in U.S. Pat. No. 4,144,317, which is incorporated herein by reference. Typically the drug is dispersed through the matrix or carrier at a concentration in excess of saturation, the amount of the excess being a function of the intended useful life of the system. The drug, however, may be present at initial levels below saturation without departing from this invention.

In addition to the drug, the passive agent reservoir 26 may also contain other materials such as permeation enhancers, dyes, pigments, inert fillers, excipients, and conventional components of pharmaceutical products or transdermal therapeutic systems as known to the art.

The passive reservoir 26, or membrane 30 if one is used, should be in firm contact with the patient's skin or mucosa when device 10 is placed on the body. Flow of drug from the passive agent reservoir 26 is metered through the reservoir matrix material in accordance with the laws of hydrodynamics or diffusion, as herein discussed, at a predetermined rate. In operation, drug molecules are continuously removed from the reservoir and diffuse to the skin or mucosa of the patient. In the case of systemic drugs, the drugs are transported through the skin or mucosa and enter circulation through the capillary network.

Turning now to the active (i.e., electrically assisted) portions of the device, the active agent reservoir 24 and the electrolyte reservoir 25 are each comprised of a hydrophilic polymer, most preferably a mixture of a hydrophilic polymer and a hydrophobic polymer, and most preferably a mixture of about 10 to 60 wt % of a hydrophilic polymer and about 10 to 60 wt % of a hydrophobic polymer on a dry weight basis. The agent reservoir matrix typically contains about 1 to 60 wt % of the agent on a dry weight basis. The electrolyte reservoir matrix typically contains about 0.5 to 60 wt % of the electrolyte on a dry weight basis.

As used herein, a hydrophilic polymer is a polymer having an equilibrium water content of at least 20 wt %, preferably at least about 30 wt % and most preferably at least about 40 wt % after prolonged exposure to an atmosphere having a relative humidity of over about 90%. Also as used herein, a hydrophobic polymer is any polymer having an equilibrium water content of less than 20 wt %, preferably less than about 15 wt % and most preferably less than about 10 wt % after prolonged exposure to an atmosphere having a relative humidity of over about 90%.

Preferably, the hydrophobic polymer is heat fusible and can be heat fused to another polymeric surface such as a polymer based electrode or a membrane. Alternatively, if the electrode is composed of a metal, such as a metal plate, a metal foil or a metallized surface on a suitable backing material, the hydrophobic polymer may require a resinous tackifying agent.

Suitable hydrophobic polymers for use in the matrix of reservoirs 24 and 25 include, without limitation, polyethylene, polypropylene, polyisoprenes and polyalkenes, rubbers, copolymers such as Kraton®, polyvinylacetate, ethylene vinyl acetate copolymers, polyamides such as nylons, polyurethanes, polyvinylchloride, acrylic or methacrylic resins such as polymers of esters of acrylic or methacrylic acid with alcohols such as n-butanol, n-pentanol, isopentanol, 2-methyl butanol, 1-methyl butanol, 1-methyl pentanol, 2-methyl pentanol, 3-methyl pentanol, 2-ethyl butanol, isooctanol, n-decanol, or n-dodecanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butylacrylamide, and iraconic acid, N-branched alkyl maleamic acids wherein the alkyl group has 10–24 carbon atoms, glycol diacrylates, and blends thereof. Most of the above listed hydrophobic polymers are heat fusible. Of these, polyisobutylene rubbers and ethylene vinyl acetate copolymers are preferred.

In cases where the electrode is a metal foil or a metallized polymeric film, it may be necessary to add a tackifying resin to the hydrophobic polymer component in order to enhance its adhesiveness. Suitable hydrophobic polymers which can be rendered more adhesive by the addition of tackifying resins include, without limitation, cellulose acetate, cellulose acetate butyrate, ethylcellulose, polyurethanes, poly-(styrene-butadiene) and poly(styrene-isoprene-styrene) block copolymers, ethylene vinyl acetate copolymers such as those which are described in U.S. Pat. No. 4,144,317, plasticized or unplasticized polyvinylchloride, natural or synthetic rubbers, $C_2$–$C_4$ polyolefins such as polyethylene, polyisoprene, polyisobutylene and polybutadiene. Examples of suitable tackifying resins include, without limitation, fully hydrogenated aromatic hydrocarbon resins, hydrogenated esters and low molecular weight grades of polyisobutylene. Particularly suitable are tackifiers sold by Hercules, Inc. of Wilmington, Del. under the trademarks Staybelite Ester®#5 and #10, Regal-Rez® and Piccotac®.

Suitable hydrophilic polymers for use in the matrix of reservoirs 24 and 25 include polyvinylpyrrolidones, polyvinyl alcohol, polyethylene oxides such as Polyox® manufactured by Union Carbide Corp., Carbopol® manufactured by BF Goodrich of Akron, Ohio; blends of polyoxyethylene or polyethylene glycols with polyacrylic acid such as Polyox® blended with Carbopol®, polyacrylamide, Klucel®, cross-linked dextran such as Sephadex (Pharmacia Fine Chemicals, AB, Uppsala, Sweden), Water Lock® (Grain Processing Corp., Muscatine, Iowa) which is a starch-graft-poly(sodium acrylate-co-acrylamide) polymer, cellulose derivatives such as hydroxyethyl cellulose, hydroxypropylmethylcellulose, low-substituted hydroxypropylcellulose, and cross-linked Na-carboxymethylcellulose such as Ac-Di-Sol (FMC Corp., Philadelphia, Pa.), hydrogels such as polyhydroxyethyl methacrylate (National Patent Development Corp.), natural gums, chitosan, pectin, starch, guar gum, locust bean gum, and the like, along with blends thereof. Of these, polyvinylpyrrolidones are preferred.

Blending of the drug or electrolyte with the polymer matrix is done mechanically, either in solution or by milling, extrusion or hot melt mixing, for example. The resulting reservoir layers may then be prepared by solvent casting, extrusion or by melt processing, for example.

In addition to the drug and electrolyte, the reservoirs 24 and 25 may also contain other conventional materials such as dyes, pigments, inert fillers, and other excipients.

Layer 21 preferably contains electrical circuitry for controlling the level, polarity, timing, pulsing frequency, duty cycle, etc, of current produced by device 10. The control circuit may take the form of an on-off switch for "on-demand" drug delivery (e.g., patient controlled delivery of an analgesic for pain relief), a timer, a fixed or variable electrical resistor, a controller which automatically turns the device on and off at some desired periodicity to match the natural or circadian patterns of the body, or other more sophisticated electronic control devices known in the art. For example, it may be desirable to deliver a predetermined constant level of current from device 10 since a constant current level ensures that the active agent is delivered through the skin at a constant rate. The current level can be controlled by a variety of known means, for example, a resistor or a simple circuit that employs a resistor and a field effect transistor. Control circuit may also include an integrated circuit which could be designed to control the dosage of active agent, or even to respond to sensor signals in order to regulate the dosage to maintain a predetermined dosage regimen. A relatively simple circuit can control the current as a function of time, and if desired, generate complex current waveforms such as pulses or sinusoidal waves. In addition, the control circuit 19 may employ a bio-feedback system which monitors a biosignal, provides an assessment of the therapy, and adjusts the active agent delivery accordingly. A typical example is the monitoring of the blood sugar level for controlled administration of insulin to a diabetic patient.

Figure 2:
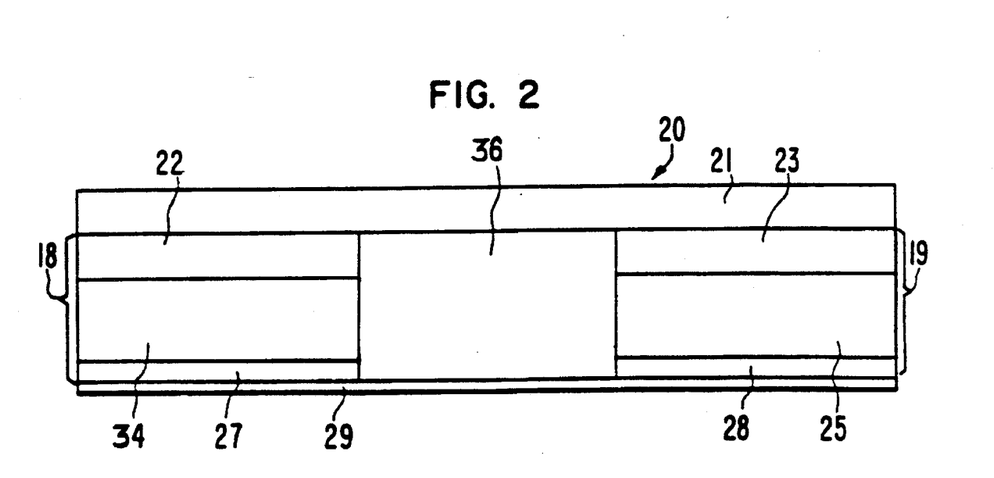
FIG. 2 is a schematic view of another embodiment of a transdermal drug delivery device according to the present invention.

As an alternative to the side-by-side alignment of the donor electrode assembly 18, the passive agent reservoir 26 and the counter electrode assembly 19 shown in FIGS. 1 and 2, the electrode assemblies can be concentrically aligned with the counter electrode assembly 19 positioned centrally and surrounded by an angularly shaped passive agent reservoir 26 which is in turn surrounded by an angularly shaped donor electrode assembly 18. The electrode assemblies can, if desired, be reversed with the counter electrode assembly surrounding the centrally positioned donor electrode assembly. The concentric alignment of the electrode assemblies can be circular, elliptical, rectangular or any of a variety of geometric configurations.

The combined skin-contacting areas of electrode assemblies 18 and 19 can vary from less than 1 $cm^2$ to greater than 200 $cm^2$. The average device however, will have electrode assemblies with a combined skin-contacting area within the range of about 5–50 $cm^2$. The skin-contacting area of passive agent reservoir 26 or membrane 30 can vary from about 1 to 100 $cm^2$, and most typically from about 5 to 25 $cm^2$.

A second embodiment of the invention is shown in FIG. 2. Like the device illustrated in FIG. 1, device 20 also includes a donor electrode assembly 18 and a counter electrode assembly 19. The donor electrode assembly 18 and the counter electrode assembly 19 may be adhered to the body surface using ion-conducting adhesive layers 27 and 28, respectively. Device 20 also includes a donor electrode 22 and a counter electrode 23 which are electrically connected to layer 21 containing electrical circuitry and a power source.

Unlike device 10 illustrated in FIG. 1 however, device 20 utilizes an electrically insulating separator 36 which contains no passive agent. In device 20, both the active agent and the passive agent are contained within agent reservoir 34. If necessary or desirable, the passive agent may be placed entirely in reservoir 25 or a portion of the passive agent may be placed in each of reservoirs 25 and 34. In this embodiment of the invention, the active agent, when in the form of a liquid solution or suspension, is in the form of charged ions which are actively delivered by the electric field generated by the power source in layer 21. The passive agent contained in reservoir 34 and/or reservoir 25, when in the form of a liquid solution or suspension, is non-ionized (i.e., the passive agent is in the form of uncharged molecules) and is passively delivered through the body surface due to the concentration gradient between the high concentration of the passive agent in reservoir 24 and the low concentration of the passive agent within the body. The passive agent concentration gradient causes the passive agent to be passively delivered from reservoir 34 and/or reservoir 25 both when the power source in layer 21 is activated (and thus when the electric field is generated) and when the power source in layer 21 is turned off. Of course when the power source is turned on and the electric field through reservoirs 25 and 34 is generated, some relatively small amount of the passive agent is actively delivered by the phenomenon of electroosmosis. However, the electroosmosis flux component will typically be much smaller (e.g., less than 20%) than the passive flux component of the passive agent. Of course in cases where the active agent and the passive agent are merely different forms of the same chemical entity (e.g., the passive agent is a narcotic analgesic in the form of a non-ionic base and the active agent is an ionic (e.g., salt) form of the base), then the relative size of the electroosmotic component becomes inconsequential since the electroosmotic flux component of the passive agent can be considered merely a portion of the total electrically assisted flux. However, in cases where the active agent and the passive agent are not chemically related (e.g., the passive agent is an anti-inflammatory in non-ionic form, such as ibuprofen, and the active agent is an antibiotic in ionic form, such as tetracycline HCl), it is desirable to minimize the electroosmotic flux of the passive agent so that delivery of the passive agent remains substantially independent of whether or not the power source is activated. By minimizing the electroosmotic flux of the passive agent to less than 20%, and preferably less than 10%, of the passive flux of the passive agent, the delivery of passive agent from device 20 is substantially unaffected by the amount of current passing through reservoirs 25 and 34. Thus, the delivery of passive agent is substantially unaffected by the activation or deactivation of the electrical portions of the device. Also like the device in FIG. 1, the passive delivery of the passive agent may provide a baseline delivery of drug or beneficial agent which can be supplemented by activating the electrically assisted portions of the device and actively delivering the active agent.

In the second embodiment of the invention, the matrix of reservoir 34 and/or reservoir 25 preferably comprises a mixture of a hydrophilic polymer and a hydrophobic polymer. Most preferably, the active agent in reservoir 34 is an aqueous solution of a drug salt and therefore is delivered along the hydrated hydrophilic polymer pathways through reservoir 34. Likewise, the passive agent in reservoir 34 and/or reservoir 25 most preferably diffuses along the non-hydrated, hydrophobic polymer pathways through reservoirs 25 and/or 34.

This invention has utility in connection with the delivery of drugs within the class which can be delivered through body surfaces. Of course, it will be understood from the description herein that the term "passive agent" is limited to those therapeutically active substances which are preferably in the form of neutral, uncharged molecules and which are able to passively diffuse through a matrix and/or membrane and through a body surface at a therapeutically effective rate. Similarly, the term "active agent" is limited to therapeutically active substances which are preferably in the form of charged ions and which are able to be delivered through a body surface by iontophoresis at therapeutically effective rates. As used herein, the expressions "agent" and "drug" are used interchangeably and are intended to have their broadest interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine and ondansetron, antinauseants, antineoplastics, antiparkinsonism drugs, cardiostimulants such as dobutamine, antipruritics, antipsychotics, antipyretics, antispasmodics, including gastrointestinal and urinary, anticholinergics, sympathomimetrics, xanthine derivatives, cardiovascular preparations including calcium channel blockers such as nifedipine, beta-blockers, beta-agonists such as salbutamol and ritodrine, antiarrythmics, antihypertensives such as atenolol, ACE inhibitors such as enelopril, diuretics, vasodilators, including general, coronary, peripheral and cerebral, central nervous system stimulants, cough and cold preparations, decongestants, diagnostics, hormones such as parathyroid hormone, hypnotics, immunosuppressives, muscle relaxants, parasympatholytics, parasympathomimetrics, prostaglandins, proteins, peptides, psychostimulants, sedatives and tranquilizers.

The invention is also useful in the active delivery of peptides, polypeptides, proteins and other macromolecules. These macromolecular substances typically have a molecular weight of at least about 300 daltons, and more typically a molecular weight in the range of about 300 to 40,000 daltons. Specific examples of peptides and proteins in this size range include, without limitation, LHRH, LHRH analogs such as buserelin, gonadorelin, nafarelin and leuprolide, GHRH, GHRF, insulin, insulotropin, heparin, calcitonin, octreotide, endorphin, TRH, NT-36 (chemical name: N=[[(s)-4-oxo-2-azetidinyl]carbonyl]-L-histidyI-L-prolinamide), liprecin, pituitary hormones (e.g., HGH, HMG, HCG, desmopressin acetate, etc), follicle luteoids, $\alpha$ANF, growth factors such as growth factor releasing factor (GFRF), $\beta$MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirulog, hyaluronidase, interferon, interleukin-1, interleukin-2, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 antitrypsin (recombinant), and TGF-beta.

Having thus generally described the invention, the following examples will illustrate preferred embodiments thereof.

EXAMPLE I

A therapeutic system designed to transdermally deliver fentanyl, a narcotic analgesic, has a configuration similar to that illustrated in FIG. 1 and is made of the following materials. The anodic donor electrode 22 is composed of a polymer matrix containing silver particles. The electrode is made by mixing powdered silver and cross-linked polyvinylpyrrolidone into a polyisobutylene matrix. The anodic donor electrode is comprised of 27.5 g polyisobutylene (PIB) having a molecular weight of 1,200,000 (sold by Exxon Corp. of Irving, Tex.), 27.5 g of PIB having a molecular weight of 35,000 (sold by Exxon Corp.), 20 g of polyvinylpyrrolidone (PVP-XL 10 sold by GAF Corp. of Wayne, N.J.) and having a degree of cross-linking of 10%, and 25 g of silver powder having an average particle size of about 8 microns. The active agent reservoir 24 is composed of 32.5 wt % PIB (molecular weight of 1,200,000), 32.5 wt % PIB (molecular weight of 35,000), 25 wt % PVP-XL 10 and 10 wt % fentanyl HCl. Fentanyl HCl is water soluble. Thus, when the active agent reservoir 24 is hydrated, the fentanyl salt dissolves to form fentanyl drug ions (cations) and chloride counter ions (anions).

The ion-conducting adhesive layers 27 and 28 are composed of 16 wt % PIB (molecular weight of 1,200,000), 64 wt % PIB (molecular weight of 35,000), and 20 wt % PVP-XL 10. The counter electrode assembly 19 has substantially the same composition as the donor electrode assembly except the cathodic counter electrode 23 contains 25 wt % AgCl in place of the silver and the electrolyte reservoir 25 contains 10 wt % NaCl in place of fentanyl HCl. The skin contacting area of each of the electrode assemblies 18 and 19 is 10 cm$^2$.

The electronic layer 21 contains three 3-volt lithium button-cell batteries arranged in series and electrically connected between the donor electrode 22 and the counter electrode 23. An on-off switch is provided as a means for activating the electrically assisted (i.e., active delivery) portions of the device. When activated, the power source, in combination with a current controller, provides a current of 0.6 mA (i.e., a current density of 60 $\mu$A/cm$^2$) which is sufficient to deliver about 25 pg of fentanyl over a period of 5 minutes.

The passive (i.e., non-electrically assisted) delivery portion of the device is comprised of the passive drug reservoir 26 and a rate controlling membrane 30. The passive drug reservoir 26 has an aqueous gel core with a backing layer comprised of a multilaminate of polyethylene, aluminum, polyester and ethylene vinyl acetate copolymer. The exterior surface of the backing layer is in contact with electrode assembly 18, electrode assembly 19 and the bottom surface of layer 21. The multilaminate backing layer provides an insulting layer between electrode assemblies 18 and 19.

The aqueous gel core of passive drug reservoir 26 is composed of 1 wt % fentanyl base, 2 wt % hydroxyethylcellulose and 97 wt % of a 25% solution of ethanol in water. Fentanyl base is in the form of neutral, uncharged molecules. The flux control membrane 30 is composed of an ethylene vinyl acetate copolymer having a vinyl acetate content of 9%. A layer of silicone adhesive, having a thickness of 2 mils, is applied to the skin side of the flux control membrane 30. The passive drug reservoir 26 has a skin contacting area of 10 cm, and releases fentanyl base at the rate of 25 $\mu$g/hr.

The fentanyl delivery system provides a base line fentanyl base delivery rate of 25 $\mu$g/hr from the passive drug reservoir 26. The electrically assisted portions of the device enable the system to deliver a bolus of 25 $\mu$g of ionic fentanyl every 5 minutes while the electrically assisted portion is in operation. Thus, when the electrically assisted portions are activated, the total fentanyl delivery rate from the system is about 325 $\mu$g/hr.

EXAMPLE II

A therapeutic system designed to transdermally deliver both fentanyl by passive delivery and metoclopramide by active delivery has a configuration similar to that illustrated in FIG. 12 and is made of the same materials used in the device of Example I with the following exceptions. First, the active drug reservoir 24 is composed of 20 wt % PIB (molecular weight of 1,200,000), 20 wt % PIB (molecular weight of 35,000), 35 wt % of metoclopramide HCl and 25 wt % PVP-XL 10. Metoclopramide HCl is water soluble. Thus, when the active drug reservoir 24 is hydrated the metoclopramide salt dissolves and forms metoclopramide drug ions (cations) and chloride counter ions (anions). The donor electrode assembly 18 and the counter electrode assembly 19 each have a skin contacting area of 15 cm². The current applied by the electrically assisted portions of the device is 1.5 mA.

The device delivers fentanyl base passively from the passive drug reservoir 26, similar to the device described in Example I. The passive non-ionic fentanyl base delivery rate is 25 µg/hr. The electrically assisted portions of the device deliver ionic metoclopramide at a rate of about 25 mg metoclopramide per day.

EXAMPLE III

A therapeutic system designed to transdermally deliver sufentanil base by passive delivery and sufentanil HCl by active delivery has a configuration similar to that illustrated in FIG. 2. Sufentanil (both the base and salt forms) is a narcotic analgesic. The anodic donor electrode 22 and the cathodic counter electrode 23 have the same composition as described in Example I. Likewise, the ion-conducting adhesive layers 27 and 28, as well as the electrolyte reservoir 25 have the same composition as described in Example I. Separator 36 is composed of an ethylene vinyl acetate copolymer having a vinyl acetate content of 40% (EVA 40). EVA 40 is substantially impermeable to the passage of ionics species and therefore acts as an insulator between electrode assemblies 18 and 19.

Reservoir 34 contains both sufentanil base, which is in the form of neutral uncharged molecules and therefore is delivered passively, and sufentanil hydrochloride, which upon hydration of reservoir 34, dissolves to form sufentanil cations which are actively delivered. The reservoir 34 is prepared by adding 25 g low molecular weight PIB (average molecular weight of 35,000) and 25 g high molecular weight PIB (average molecular weight 1,200,000) to a stirring vessel. Light mineral oil (MO) is added to the same vessel with a ratio of approximately 1.125 to 1 part of PIB. Heptane is added and the mixture is stirred until the polymers are dissolved. 25 wt % sufentanil base is added to the solution to generate a blend of sufentanil base in the PIB/MO.

Separately, 15 g of PVP-XL 10 and 10 g of sufentanil HCl are added to a stirring vessel. The mixture is stirred until the sufentanil salt is well blended in the PVP-XL 10. The PVP-sufentanil salt blend is then added to the PIB/MO sufentanil base blend and intimately mixed.

The device delivers non-ionic sufentanil base passively from reservoir 34. In addition, when the power source is activated, the device delivers ionic sufentanil actively from reservoir 34. The passive sufentanil base delivery rate is 5 µg/hr. The electrically assisted ionic sufentanil delivery rate is 30 µg/hr when the power source is turned on. This device is suitable for delivering a baseline level (e.g., 5 µg/hr) of sufentanil for the treatment of chronic pain, with the option of providing higher, patient activated delivery during episodes of severe pain.

Having thus generally described our invention and described in detail certain preferred embodiments thereof, it will be readily apparent that various modifications to the invention may be made by workers skilled in the art without departing from the scope of this invention and which is limited only by the following claims.

We claim:
1. A transdermal agent delivery device, comprising:
an agent reservoir adapted to be placed in agent transmitting relation with a body surface and positioned within an electric field generated by electrically connecting the agent reservoir to a source of electrical power, the agent reservoir containing:
a sufficient amount of a passively transported agent to achieve a therapeutically effective passive flux of the passive agent from the reservoir to, and through, a body surface when the reservoir is placed in passive agent transmitting relation with the body surface; and
a sufficient amount of an actively transported agent to achieve a therapeutically effective electrically assisted flux of the active agent from the reservoir to, and through, a body surface when the reservoir is placed in active agent transmitting relation with the body surface and an electric field is generated through said reservoir.

2. The device of claim 1, wherein the active agent is ionized and the passive agent is nonionized.

3. The device of claim 1, including means for electrically connecting and electrically disconnecting the power source and the agent reservoir.

4. The device of claim 3, wherein the means for electrically connecting and electrically disconnecting comprises an on-off switch.

5. The device of claim 2, wherein the ionized actively transported agent comprises an aqueous salt solution.

6. The device of claim 2, wherein the actively transported agent comprises an ionized form of the passively transported nonionized agent.

7. The device of claim 1, wherein the passively transported agent is an acid or a base and the actively transported agent is a salt of the acid or base.

8. The device of claim 1, wherein the actively transported agent and the passively transported agent are narcotic analgesics.

9. The device of claim 1, wherein the active agent reservoir is comprised at least in part of a hydrophilic polymer matrix containing the active agent.

10. The device of claim 1, wherein the agent reservoir comprises a donor reservoir of an iontophoretic delivery device.

11. The device of claim 1, wherein the agent reservoir comprises the donor and counter reservoirs of an iontophoretic delivery device.

12. The device of claim 11, wherein the counter reservoir is substantially free of the actively transported agent.

13. A method of delivering an agent transdermally comprising:
a) placing a reservoir containing a sufficient amount of an actively transported agent to achieve a therapeutically effective electrically assisted flux of the active agent from the reservoir to, and through, a body surface when the reservoir is placed in active agent transmitting relation with a body surface;
b) placing a reservoir containing a passively transported agent to achieve a therapeutically effective passive flux of the passive agent from the reservoir to, and through, a body surface when the reservoir is placed in passive agent transmitting relation with a body surface to passively transport said passive agent through the body surface; and
c) generating an electric field at least through the reservoir containing the actively transported agent to actively transport said agent through the body surface.

14. The method of claim 13, including periodically deactivating the electric field to stop the active transport of the active agent.

15. The method of claim 13, wherein the active agent is ionized and the passive agent is nonionized.

16. The method of claim 13, wherein the active agent comprises an aqueous salt solution.

17. The method of claim 13, wherein the active agent comprises a salt of the passive agent.

18. The method of claim 13, wherein the passive agent is an acid or a base and the active agent is a salt of the acid or base.

19. A method of treating chronic pain characterized by periodic episodes of more severe pain, comprising:
   a) placing in a reservoir a sufficient amount of a nonionized narcotic analgesic to achieve a chronic pain reducing passive flux of the nonionized narcotic analgesic through a body surface of a patient when the reservoir is placed in narcotic analgesic transmitting relation with the body surface;
   b) placing in the reservoir a sufficient amount of an ionized narcotic analgesic to achieve a severe pain reducing combined flux of the narcotic analgesics, the combined flux being comprised of an electrically assisted flux of the ionized narcotic analgesic and a passive flux of the nonionized narcotic analgesic;
   c) generating an electric field through the reservoir when the patient experiences an episode of severe pain.

20. The method of claim 19, wherein the ionized narcotic analgesic comprises a salt of fentanyl or sufentanil.

21. The method of claim 19, wherein the nonionized narcotic analgesic comprises fentanyl base or sufentanil base.

22. A method of delivering an ionized actively transported agent and a nonionized passively transported agent through a body surface of a patient, comprising:
   a) placing an amount of the nonionized passively transported agent in a reservoir, the amount of nonionized agent being sufficient to achieve a therapeutic passive flux of the nonionized agent from the reservoir to, and through, the body surface when the reservoir is placed in agent transmitting relation with the body surface;
   b) placing an amount of the ionized actively transported agent in the reservoir, the amount of ionized agent being sufficient to achieve a therapeutic electrically assisted flux of the ionized agent from the reservoir to, and through, the body surface when the reservoir is placed in agent transmitting relation with the body surface and an electric field is generated through the reservoir;
   c) placing the reservoir in agent transmitting relation with the body surface to passively transport said nonionized agent through the body surface at a therapeutic passive flux; and
   d) generating an electric field through the body surface at a therapeutic electrically assisted flux.

23. The method of claim 22, including periodically generating the electric field.

24. The method of claim 22, wherein the ionized agent comprises an aqueous salt solution.

25. The method of claim 22, wherein the ionized agent comprises a salt of the nonionized agent.

26. The method of claim 22, wherein the nonionized agent is an acid or a base and the ionized agent is a salt of the acid or base.

* * * * *